US012751866B2

(12) United States Patent
Granese

(10) Patent No.: US 12,751,866 B2
(45) Date of Patent: Oct. 6, 2026

(54) LYMPHATIC COMPRESSION SPACE SLEEVE

(71) Applicant: Carson Granese, St. Petersburg, FL (US)

(72) Inventor: Carson Granese, St. Petersburg, FL (US)

(*) Notice: Subject to any disclaimer, the term of this patent is extended or adjusted under 35 U.S.C. 154(b) by 0 days.

(21) Appl. No.: 19/044,024

(22) Filed: Feb. 3, 2025

(65) Prior Publication Data

US 2026/0224407 A1 Aug. 6, 2026

(51) Int. Cl.
*A61F 13/10* (2006.01)
*A61H 23/02* (2006.01)

(52) U.S. Cl.
CPC ......... *A61F 13/10* (2013.01); *A61H 23/0263* (2013.01); *A61H 2023/0272* (2013.01)

(58) Field of Classification Search
CPC ........ A61F 5/30; A61F 5/0111; A61F 13/085; A61H 9/0078; A61H 2011/005; A61H 2201/5061; A61H 2023/0272; A61H 23/0263; A61H 11/00; A61H 2201/5056; A61H 2201/5053; A61H 2209/00; A61B 5/4528; A61B 5/1038; A61B 5/1071; A61B 5/6807
See application file for complete search history.

(56) References Cited

U.S. PATENT DOCUMENTS

| | | | | |
|---|---|---|---|---|
| 2009/0143704 A1* | 6/2009 | Bonneau | A61F 5/0111 | 600/595 |
| 2009/0299239 A1* | 12/2009 | Meyer | A61H 11/00 | 601/149 |
| 2016/0089299 A1* | 3/2016 | Munoz | A61H 23/0263 | 601/70 |
| 2023/0346605 A1* | 11/2023 | Carroll | A61H 11/00 | |

FOREIGN PATENT DOCUMENTS

| | | | | |
|---|---|---|---|---|
| GB | 2612313 A | * | 5/2023 | A61H 9/0092 |
| KR | 20230064320 A | * | 5/2023 | A61F 13/085 |
| KR | 20240081593 A | * | 6/2024 | A61H 39/04 |

OTHER PUBLICATIONS

Compression Management Services, Bio-Compression Systems Sequential Circulator, https://www.compressionmanagement.com/about-us/, 2025, accessed Apr. 30, 2025 (4 pages).

(Continued)

*Primary Examiner* — Ophelia A Hawthorne
(74) *Attorney, Agent, or Firm* — Wilmer Cutler Pickering Hale and Dorr LLP

(57) ABSTRACT

Disclosed herein is a Lymphatic Compression Space Sleeves ("LCSS") for promoting lymph circulation and treating lymphedema in a human subject. The LCSS includes (i) a compression device; (ii) a force sensor; (iii) a vibrational motor; and (iv) a controller, and can be fitted onto a body part, e.g., an arm, of a human subject to help promote lymph circulation throughout the human subject's body. The LCSS can be particularly useful in space, where the microgravity (Continued)

environment can cause poor lymph circulation and lead to swelling and/or lymphedema. Also disclosed herein are methods for promoting lymph circulation and treating lymphedema in a human subject.

16 Claims, 6 Drawing Sheets

(56) References Cited

OTHER PUBLICATIONS

Nooro, Multi-Functional Electrical Massager, https://nooro-us.com/products/whole-body-massagertm-muscle-pain-relief-device, 2022, accessed Apr. 30, 2025 (27 pages).
Tactile Medical, Lymphedema Solutions, https://tactilemedical.com/our-lymphedema-solutions/, 2023, accessed Apr. 30, 2025 (10 pages).

* cited by examiner

LYMPHATIC COMPRESSION SPACE SLEEVE

FIELD OF THE INVENTION

This invention relates to devices and methods for improving lymphatic circulation in a human subject. The invention also includes methods of treating or preventing lymphedema. The invention is particularly suited for use in low or microgravity environments, e.g., in space.

BACKGROUND OF THE INVENTION

It is essential for astronauts to maintain a healthy body in space. Diet and exercise are priorities for NASA development. One issue that can affect astronauts in space is poor lymph circulation. The lymphatic system is an important part of the human body's immune system. It is comprised of a network of organs, nodes, and vessels that circulate lymph throughout the system. Lymph comes from blood plasma and contains proteins, fats, and white blood cells. The lymphatic system transports lymph from different tissues around the body back into the blood stream, destroys damaged blood cells, and creates new blood cells.

In the typical gravity environment on Earth, gravity aids in lymph circulation by pushing fluid down. However, in space, the reduced gravity can cause less lymph fluid to reach the legs and more to stay in the upper area of the body. This can be especially problematic because arms do not have the same capability for reducing lymph as other areas in the body given that there is usually no lymph build-up in the upper body in Earth's gravitational environment. The decreased gravitational force also causes less pressure to pump lymph throughout the system, which can lead to swelling. If the swelling becomes severe enough, it can prevent astronauts from being able to perform essential functions and may even prevent them from being able to fit in their space suits. The issue of poor lymph circulation is likely to become worse as humans look to travel further into space, such as to Mars.

Poor lymph circulation can also lead to lymphedema, which is a condition that involves an abnormal build-up of lymph in the body and occurs when lymph cannot properly flow throughout the body. Lymphedema can cause swelling in a particular area, such as the arms or legs, difficulty breathing, and a tight feeling in the skin. Severe cases of lymphedema may lead to increased risk of skin infections and sepsis, and may even lead to skin changes and breakdown.

There are existing methods for treating lymphedema on Earth. However, due to the low gravity environment in space inverting many systems in the body, solutions are much more limited. Additionally, many of these treatments involve large and bulky equipment that would be difficult to bring into space, and are often only used once the problems have become severe. Therefore, there exists a need for devices and methods for promoting lymph circulation and treating lymphedema in a human subject in space.

SUMMARY OF THE INVENTION

The invention provides devices and methods for promoting lymph circulation and treating lymphedema in a human subject, especially human subjects who are exposed to low gravity environments.

In one aspect, the invention is directed to a system that detects the build-up of lymph in a human subject's body and promotes circulation of the lymph in response to the build-up. The system can advantageously be programmed to automatically promote lymph circulation in response to the detection of lymph build-up without requiring any manual input from the user. In one aspect, the invention is directed to a device for promoting circulation of lymphatic fluid in a human subject including: (i) a compression device fitted to a body part of the human subject, e.g., an arm; (ii) a force sensor configured to detect a force exerted by the body part of the human subject; (iii) a vibrational motor; and, optionally, (iv) a controller; wherein the controller is configured to activate the vibrational motor in response to the force sensor detecting the force above a predetermined threshold. In some embodiments, the compression device is a compression bandage. In other embodiments, the compression device may be a cast, a brace, or an inflatable garment that provides compression to the human subject's body part when inflated. For example, the compression bandage can be an elastic tubular bandage. In some embodiments, the compression device is comprised of a material selected from cotton, Nylon, and/or spandex. In some embodiments, the compression device is a compression sleeve. In some embodiments, the compression device is made, at least in part, from an elastic material.

The force sensor included in the device can be a force-sensing resistor. In other embodiments, the force sensor can be a strain gauge force sensor, a piezoelectric force sensor, a hydraulic force transducer, a capacitive force sensor, an optical force sensor, a magnetoelastic force sensor, or an inductive force sensor. In some embodiments, the force exerted by the body part of the human subject is a result of swelling of the body part of the human subject. The swelling can be caused by build-up of lymphatic fluid and/or lymphedema.

The device for promoting circulation of lymphatic fluid may include one or a plurality or force sensors. In some embodiments, the predetermined threshold for too much force corresponds to a resistance above about 600 k Ω. In some embodiments, the plurality of force sensors includes at least one force-sensing resistors. In some embodiments, the controller activates the vibrational motor in response to at least one of the plurality of force sensors detecting the force above the predetermined threshold, e.g., a resistance above about 600 kΩ. In other embodiments, the controller activates the vibrational motor in response to all of the plurality of force sensors detecting the force above the predetermined threshold, e.g., a resistance above about 600 kΩ.

Furthermore, the device for promoting circulation of lymphatic fluid may include one or a plurality of vibrational motors, e.g., a coin-type vibrational motor. In other embodiments, the vibrational motor can be a linear resonant actuator motor, an eccentric rotating mass vibration motor, an enclosed vibration motor, a linear magnetic ram motor, or a piezoelectric actuator. In some embodiments, all of the plurality of vibrational motors are activated simultaneously. In other embodiments, each of the plurality of vibrational motors is activated individually with a time delay, e.g., of three seconds, between each activation. In further embodiments, each of the plurality of vibrational motors is activated in pairs, with a time delay, e.g., of three seconds, between the activation of each pair. In some embodiments, the controller deactivates the vibrational motor after the force detected by the force sensor falls to a value lower than the predetermined threshold, e.g., about 600 kΩ.

In another aspect, the invention is directed to a method of promoting circulation of lymphatic fluid in a human subject including fitting a device onto a body part of the human subject, wherein the device includes: (i) a compression device fitted to the body part of the human subject; (ii) a force sensor configured to detect a force exerted by the body part of the human subject; (iii) a vibrational motor; and, optionally, (iv) a controller; wherein the method includes activating the vibrational motor in response to the force sensor detecting the force above a predetermined threshold. In some embodiments, the method includes treating lymphedema in the human subject. The human subject may be in a reduced gravity environment, and in particular embodiments, may be a human astronaut. In some embodiments, the method is used in combination with an additional therapy for treating lymphedema or promoting circulation of lymph fluid, such as exercise, drug therapy, or laser therapy.

The method may involve fitting the device to the arm of a human subject. In some embodiments, the compression device is a compression bandage. In other embodiments, the compression device may be a cast, a brace, or an inflatable garment that provides compression to the human subject's body part when inflated. In some embodiments, the compression bandage is an elastic tubular bandage. In some embodiments, the compression device is comprised of a material selected from cotton, Nylon, and/or spandex. For example, the compression device may be a compression sleeve. In some embodiments, the compression device is made, at least in part, from an elastic material.

The force sensor included in the device can be a force-sensing resistor. In other embodiments, the force sensor can be a strain gauge force sensor, a piezoelectric force sensor, a hydraulic force transducer, a capacitive force sensor, an optical force sensor, a magnetoelastic force sensor, or an inductive force sensor. In some embodiments, the force exerted by the body part of the human subject is a result of swelling of the body part of the human subject. The swelling can be caused by build-up of lymphatic fluid and/or lymphedema.

The device for promoting circulation of lymphatic fluid may include one or a plurality or force sensors. In some embodiments, the predetermined threshold for too much force corresponds to a resistance above about 600 k Ω. In some embodiments, the plurality of force sensors includes at least one force-sensing resistors. In some embodiments, the controller activates the vibrational motor in response to at least one of the plurality of force sensors detecting the force above the predetermined threshold, e.g., a resistance above about 600 kΩ. In other embodiments, the controller activates the vibrational motor in response to all of the plurality of force sensors detecting the force above the predetermined threshold, e.g., a resistance above about 600 k Ω.

Furthermore, the device for promoting circulation of lymphatic fluid may include one or a plurality of vibrational motors, e.g., a coin-type vibrational motor. In other embodiments, the vibrational motor can be a linear resonant actuator motor, an eccentric rotating mass vibration motor, an enclosed vibration motor, a linear magnetic ram motor, or a piezoelectric actuator. In some embodiments, all of the plurality of vibrational motors are activated simultaneously. In other embodiments, each of the plurality of vibrational motors is activated individually with a time delay, e.g., of three seconds, between each activation. In further embodiments, each of the plurality of vibrational motors is activated in pairs, with a time delay, e.g., of three seconds, between the activation of each pair. In some embodiments, the controller deactivates the vibrational motor after the force detected by the force sensor falls to a value lower than the predetermined threshold, e.g., about 600 k Ω.

BRIEF DESCRIPTION OF THE DRAWINGS

The following figures depict illustrative embodiments of the invention in which like reference numerals refer to like elements. These depicted embodiments may not be drawn to scale and are to be understood as illustrative of the invention and not as limit.

DETAILED DESCRIPTION

The embodiments described herein provide devices and methods for promoting lymph circulation and treating lymphedema in a human subject.

Overview of the Lymphatic Compression Space Sleeve

A Lymphatic Compression Space Sleeve ("LCSS") described herein is a device for improving lymph circulation, reducing swelling caused by build-up of lymph, and treating lymphedema. In certain embodiments, the LCSS automatically detects a build-up of lymph in a human subject's body and then causes the lymph to circulate throughout the body. The LCSS includes four main components: (i) a compression device; (ii) a force sensor; (iii) a vibrational motor; and, optionally, (iv) a controller. Advantageously, the components of the LCSS can be assembled with a heat seal around any connecting wires to provide insulation, abrasion resistance, and general protection for the wires. The compression device of the LCSS can be fitted onto the body part of a human subject and, along with the vibrational motor, promote the circulation of lymph in that body part and throughout the human subject's body. The vibrational motors may be automatically activated by the controller if the LCSS detects swelling in the human subject's body part via the force sensors. The LCSS may also automatically deactivate the vibrational motors once it detects that the swelling has reduced. In some embodiments, the LCSS can also be configured to be used with Artificial Intelligence (AI).

Figure 1:
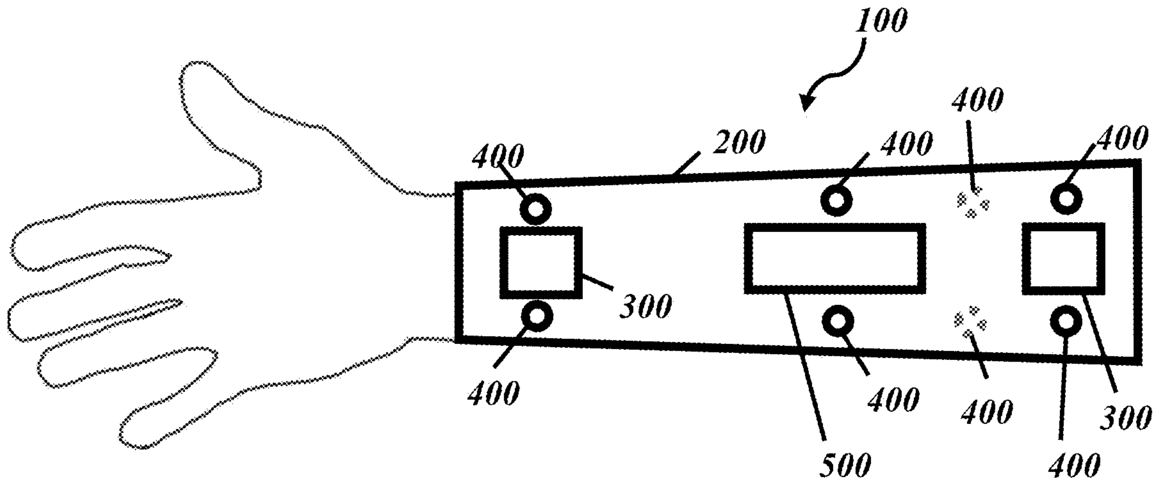
FIG. 1 is a schematic depicting an embodiment of a Lymphatic Compression Space Sleeve ("LCSS"). The schematic depicts the LCSS from a top view. Components depicted with a dotted outline show the components that are on the underside of the device which are not visible from the top view.

FIG. 1 is a schematic showing an exemplary embodiment of a Lymphatic Compression Space Sleeve (100). In the depicted embodiment, the LCSS includes a compression device (200) having two force-sensing resistors (300), eight vibrational motors (400), and a controller (500). The compression device (200) of the LCSS is a sleeve fitted to the arm of a human subject. The two force-sensing resistors (300) are placed at the two ends of the compression sleeve and are configured to detect the force caused by swelling in the human subject's arm. When the force-sensing resistors detect a force above a set threshold, the controller (500) will then activate the vibrational motors (400), which in turn will vibrate and cause lymph circulation until the force detected by the sensors falls below the set threshold.

Compression Device

An LCSS includes a compression device (200) to which the other components (force sensors, controller, vibrational motors) are attached. The compression device can be any type of commercially available device that fits a human subject's body part and places pressure on the body part. The compression device can also be of any suitable material to provide compression without cutting off circulation in the human subject's body, such as cotton, Nylon, and/or spandex, any of which may be elastic. The compression device may be fitted to and place pressure on a human subject's arm, leg, or torso. For instance, the compression device may be a compression sleeve. The compression device may also be a cast, a brace, or an inflatable garment that provides compression to the human subject's body part when inflated.

One example of a suitable compression device is a compression bandage. The compression bandage may be a flat bandage that is wrapped around the human subject's body part, e.g., the arm, leg, or torso. The flat bandage may be made of a material that provides a short stretch to place pressure on the human subject's body.

In another example, the compression bandage is an elastic tubular bandage that fits over a human subject's arm or leg. Advantageously, the tubular bandage can come in various circumference sizes, and an appropriate size is selected depending on the size of the body part of the human subject. The circumference of the tubular bandage should be chosen so that the bandage will fit snugly over the human subject's arm or leg to ensure compression of the arm or leg while maintaining a good fit. Exemplary suitable tubular bandages may have a circumference of about 10 inches to about 22 inches, e.g., about 10 to about 12 inches, about 12 to about 14 inches, about 14 to about 16 inches, about 16 to about 18 inches, about 18 to about 20 inches, and about 20 to about 22 inches.

Force Sensors

An LCSS also includes one or more force sensors (300) that detect swelling of the human subject's body part, such as swelling caused accumulation or lack of circulation of lymph fluid. The force sensor can be any commercially available force sensor of a reasonable size to fit onto the compression device. For example, the force sensor may have a sensitivity to detect forces in the range of about 0.1 N to about 50 N, e.g., about 0.1 N to about 40 N, about 0.1 N to about 30 N, about 0.1 N to about 20 N, about 0.1 N to about 10 N, about 0.2 N to about 50 N, about 0.2 N to about 40 N, about 0.2 N to about 30 N, about 0.2 to about 20 N, about 0.2 to about 10 N about 0.5 N to about 50 N, about 0.5 N to about 40 N, about 0.5 N to about 30 N, about 0.5 N to about 20 N, and about 0.5 N to about 10 N.

The LCSS may include only one force sensor, or may include a plurality of force sensors. For example, the LCSS may include up to one, two, three, four, five, six, seven, eight, nine, or ten force sensors. In some embodiments, the LCSS may include multiple force sensors, where all of the force sensors are concentrated in one area of the compression device to detect the force exerted by one area of the human subject's body part. In other embodiments, the LCSS may include multiple force sensors that are distributed evenly across the compression device to detect the force exerted across the human subject's body part. In some embodiments, the LCSS includes force sensors at locations that correspond to locations on the body where lymph is known to deposit or build-up.

The force sensor can be a force-sensing resistor, a strain gauge force sensor, a piezoelectric force sensor, a hydraulic force transducer, a capacitive force sensor, an optical force sensor, a magnetoelastic force sensor, or an inductive force sensor. In some embodiments, the force sensor is a force-sensing resistor. One example of a force sensor suitable for use with the LCSS is the force-sensing resistor produced by Interlink Electronics®. The Interlink Electronics® force-sensing resistor has an active area of about 4 cm by about 4 cm and can detect a force within the range of about 0.2 N to about 20 N. In the embodiment of the LCSS depicted in FIG. 1, the LCSS includes two of these force-sensing resistors, with one sensor placed at one end of the compression sleeve closest to the subject's wrist, and a second sensor placed at the other end of the sleeve closest to the subject's elbow.

Vibrational Motor

An LCSS also includes one or more vibrational motors (400). The vibrational motor can be configured to automatically activate in response to the force sensors detecting swelling of the human subject's body part, or can be manually activated to vibrate when desired. The vibrational motor can be any commercially available motor, and is preferably small and lightweight enough to be used with a compression device fitted to the body part of a person. For example, the vibrational motor can be a coin-type vibrational motor, a linear resonant actuator motor, an eccentric rotating mass vibrational motor, an enclosed vibrational motor, a linear magnetic ram motor, or a piezoelectric actuator. The vibrational motor may be placed on the upper and/or lower side of the compression device. In some embodiments, the vibrational motor used with the LCSS is a coin-type vibrational motor.

The LCSS may include only one vibrational motor, or may include a plurality of vibrational motors. For example, the LCSS may include between one and twenty total vibrational motors. When the LCSS includes multiple vibrational motors, the vibrational motors may be placed on the compression device in a manner so that all of the motors are concentrated in one area of the compression device. In some embodiments, this area of concentrated vibrational motors corresponds to a location in the human subject's body that is prone to lymph build-up. In other embodiments, the LCSS may include multiple vibrational motors that are distributed evenly across the compression device to so that the vibration provided by the motors is spread across the human subject's body part. If the LCSS includes an even number of vibrational motors, the vibrational motors may be placed in pairs, with each pair distributed approximately evenly across the surface of the compression device to provide an even level of vibration across the human subject's body part.

For example, the LCSS depicted in FIG. 1 includes eight total vibrational motors, with four pairs of motors distributed approximately evenly across the surface of the compression sleeve. The vibrational motors used are coin-type vibrational motors sold by Tatoko®, which each have a speed of 12,000 RPM, a voltage of 3 V, and a current of 85 mA. The Tatoko® vibrational motor has a diameter of 10 mm and a height of 3 mm.

Controller

Lastly, the LCSS can optionally include a controller (500) that is coupled with the force sensor(s) (300) and the vibrational motor(s) (400) and controls the activation of the motor(s). The controller can be any commercially available controller that is compatible with the force sensor(s) and vibrational motor(s) used and to fit on a compression device as described herein. The controller can be electronically coupled with the force sensor(s) and vibrational motor(s), e.g., by wired or wireless communications. If the controller is coupled to the force sensor(s) and vibrational motor(s) by wired communications, the connecting wires may include a heat seal to provide insulation, abrasion resistance, and general protection for the wire. Examples of a suitable controllers for use with the LCSS include a Raspberry Pi® or an Arduino®.

The controller is preferably configured to activate the vibrational motor(s) in response to the force sensor(s) detecting a force above a predetermined threshold. The force sensor threshold should be set to a value that indicates swelling in the body part of the human subject, e.g., caused by the build-up of lymph fluid and/or lymphedema. For example, the LCSS can include one or more force-sensing resistors, and the predetermined threshold for too much force may be set to a resistance of about 400 k Ω to about 1000 k Ω, e.g., about 400 k Ω, about 500 kΩ, about 600 k Ω, about 700 k Ω, about 800 k Ω, about 900 k Ω, and about 1000 k Ω. In one example, the predetermined threshold is set to a resistance of about 600 kΩ.

If the LCSS includes one force sensor, the controller may activate the vibrational motor in response to the force sensor detecting a force above the predetermined threshold. On the other hand, if the LCSS includes more than one force sensor, the controller may activate the vibrational motor if only one of the force sensors detects a force above the threshold. In other embodiments including more than one force sensor, the controller may activate the vibrational motor if a subset of the force sensors detects a force above the threshold. In another example including more than one force sensor, the controller may activate the vibrational motor only if all of the force sensors detect a force above the threshold.

If the LCSS includes more than one vibrational motor, the controller may activate each of the vibrational motors individually, in pairs, or all simultaneously. The controller can also be programmed so that there is a time delay between the activation of the vibrational motors. If the motors are activated individually, there may be a time delay between the activation of each individual motor. In another example, if the motors are activated in pairs, there may be a time delay between the activation of each pair of motors. The time delay may be between about one second and about ten seconds, e.g., about one second, about two seconds, about three seconds, about four seconds, about five seconds, about six seconds, about seven seconds, about eight seconds, about nine seconds, and about ten seconds. In one example, the time delay is set to about three seconds.

The controller may also be programmed to deactivate the vibrational motors. For instance, the vibrational motors may be deactivated after one or more of the force sensors detect that the force has fallen below the predetermined threshold. Alternatively, the vibrational motors may also be deactivated after a set amount of time.

The controller may also be configured to use Artificial Intelligence to activate the vibrational motors. For example, the AI can be used to intelligently detect when the vibrational motors should be activated based on all of the collected force sensor readings, instead of only activating the vibrational motors when the force sensor readings cross the predetermined threshold. In some embodiments, the AI may consider trends in the force sensor readings, e.g., rise or fall of force sensor readings over time, to determine whether to activate the vibrational motors. The AI may also be able to determine when the force sensor detects an aberrant reading, e.g., caused by a defective sensor, and only activate the vibrational motors based on readings that it recognizes are not aberrant. Moreover, the AI can be used to intelligently determine the length of time for which the vibrational motors are activated instead of turning off the vibrational motors automatically once the detected force drops below the predetermined threshold. For example, the AI may determine that based on the value detected by the force sensor, the vibrational motors should be activated for a longer or a shorter amount of time to most effectively promote circulation of lymph fluid and prevent or reduce swelling.

Methods

The disclosed embodiments also include methods for promoting circulation of lymphatic fluid in a human subject. The method may include fitting the LCSS onto the human subject's body part, such as an arm, a leg, or a torso, such that the LCSS can detect a force exerted by the body part of the human subject and activate one or more vibrational motors in response. The human subject may be suffering from build-up of lymphatic fluid in the upper body of the human subject, such as in the arms or in the torso, which causes swelling. The human subject may also be suffering from lymphedema. The activation of the vibrational motors can help circulate the lymphatic fluid in the body part of the human subject, which can cause reduction of swelling in the body part and/or help to treat lymphedema. In some embodiments, the LCSS can be used in combination with one or more additional therapies for treating lymphedema or promoting circulation of lymph fluid, such as exercise, drug therapy, and/or laser therapy. Examples of suitable drugs for treating lymphedema that can be used in combination with the LCSS include ketoprofen, selenium, and tacrolimus.

In particular, the human subject may be suffering from lymph build-up as a result of being in a low gravity or microgravity environment, such as being in space. For instance, the human subject may be a human astronaut. Preexisting treatments for treating lymphedema on Earth involve large and bulky equipment, which would be difficult and expensive, if not impossible, to bring into space. Thus, one benefit of the LCSS is that the LCSS is a compact, lightweight, and inexpensive device that can be brought with an astronaut into space. Another advantage of the LCSS is that it can be programmed to automatically activate as soon as it detects a build-up of lymph fluid. This can be especially convenient because the LCSS is compact enough to fit inside an astronaut's space suit, so the astronaut can carry out their regular tasks while wearing the LCSS, and the LCSS can automatically activate as needed to promote circulation of any lymph build-up without requiring any manual input to do so.

EXAMPLES

Example 1. Effectiveness of LCSS in Promoting Circulation of Lymphatic Fluid A Lymphatic Compression Space Sleeve (LCSS) was prepared including a compression sleeve, two force sensors, eight vibrational motors, and an Arduino® as depicted in FIG. 1. The compression sleeve used was an elastic tubular bandage. The force sensors used were force-sensing resistors available from Interlink Electronics®. The vibrational motors used were coin-type vibrational motors sold by Tatoko® having a diameter of 10 mm and a height of 3 mm, and rated for a speed of 12,000 RPM, a voltage of 3 V, and a current of 85 mA.

The LCSS was tested for its effectiveness at circulating fluid out of tissue. Sponges were used to simulate tissue swollen with lymph fluid. The sponges were filled with differing amounts of liquid to represent "Earth" and "Space," where the "Earth" sponges were filled with less liquid than the "Space" sponges to mimic the swelling of lymph fluid that an astronaut would experience in space. The initial and final weights of the "Space" and "Earth" sponges used in the experiment are Tables 1 and 4. The sponges were placed in Ziploc bags, and Ziploc bags containing the sponges were placed inside the LCSS compression sleeve for testing.

The sponges were tested with the LCSS according to the following procedure. Force values (KΩ) and water released (mL) were recorded every 18 seconds.

1. Prepare sponges filled with liquid for "Earth" and "Space" trials. The "Earth" sponges were filled with liquid to represent the normal amount of force exerted by a body part while on Earth, i.e., a body part without experiencing any swelling of lymph fluid. The "Space" sponges were filled with liquid to represent the amount of force exerted by a body part experiencing swelling as a result of build-up of lymph fluid.
2. Activate the vibrational motors and determine the movement of fluid that is seen with vibrational motors.
3. Record force values initially and every 18 seconds for a total of 108 seconds per trial.
4. Record volume of water released every 18 seconds during the trial.
5. Repeat 5 times.

Figure 2A:
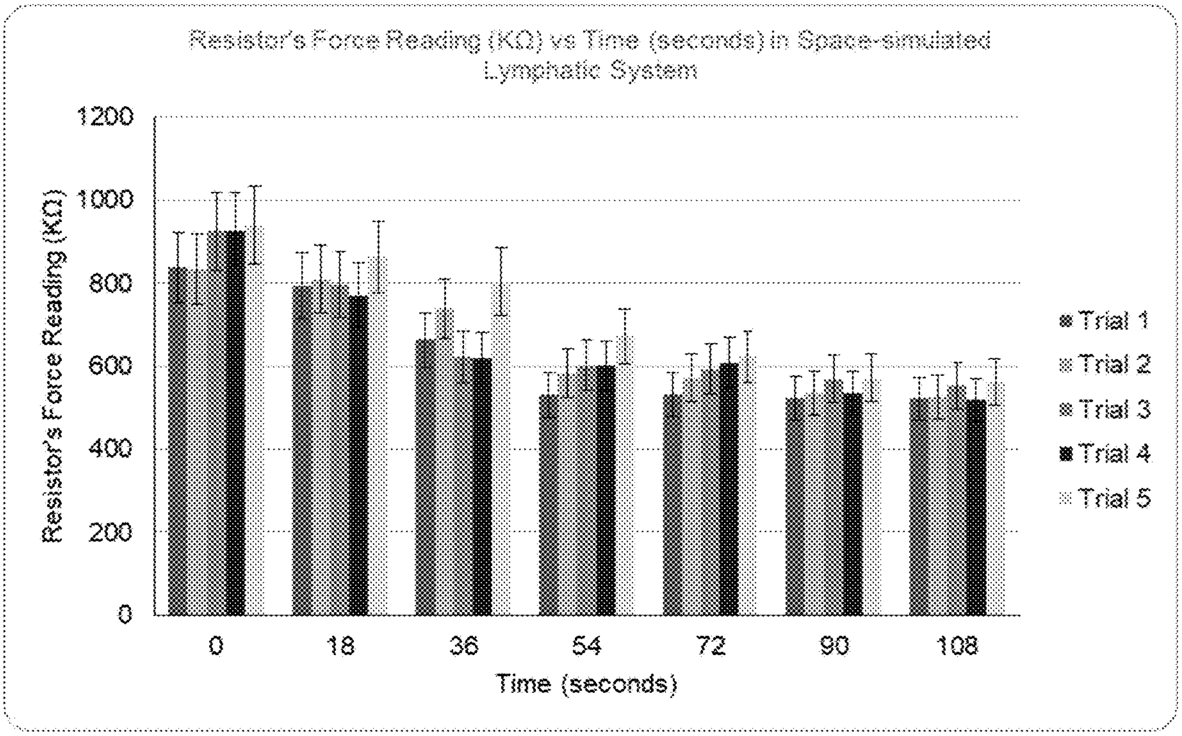
FIG. 2A is a graph showing force resistor readings (KΩ) vs. time (seconds) during the space-simulated trials described in Example 1.
Figure 2B:
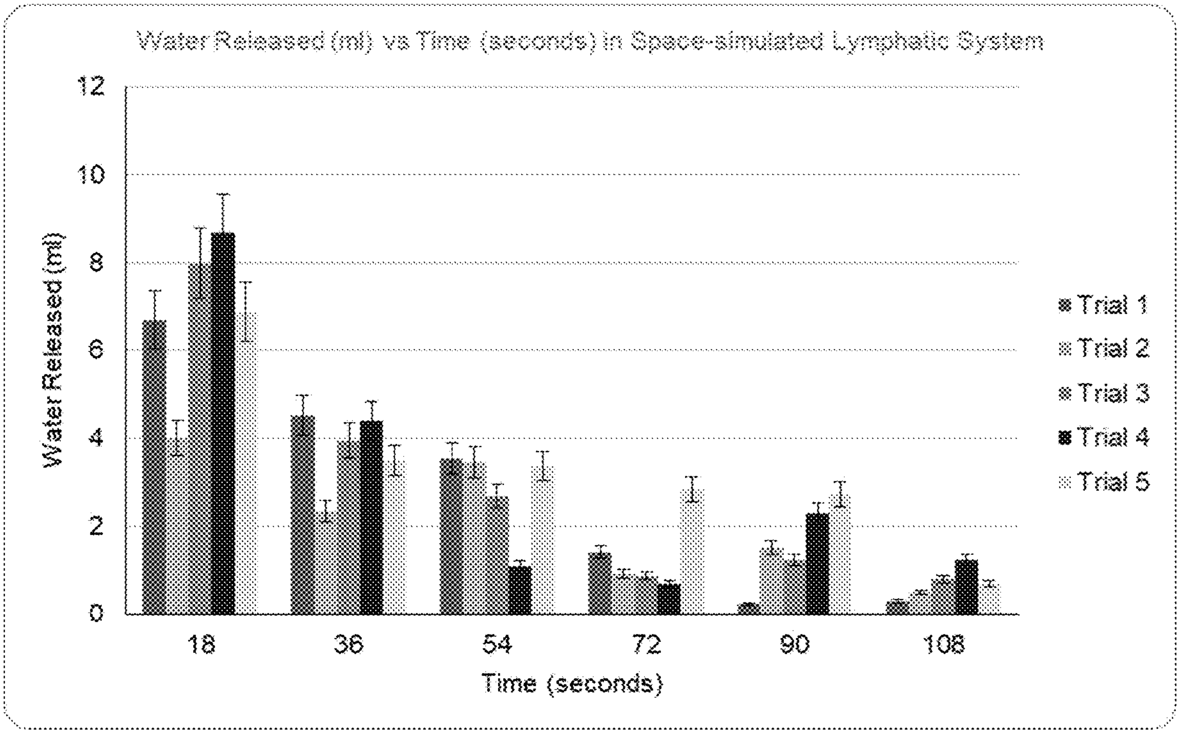
FIG. 2B is a graph showing water released (mL) vs. time (seconds) during the space-simulated trials described in Example 1.
Figure 3A:
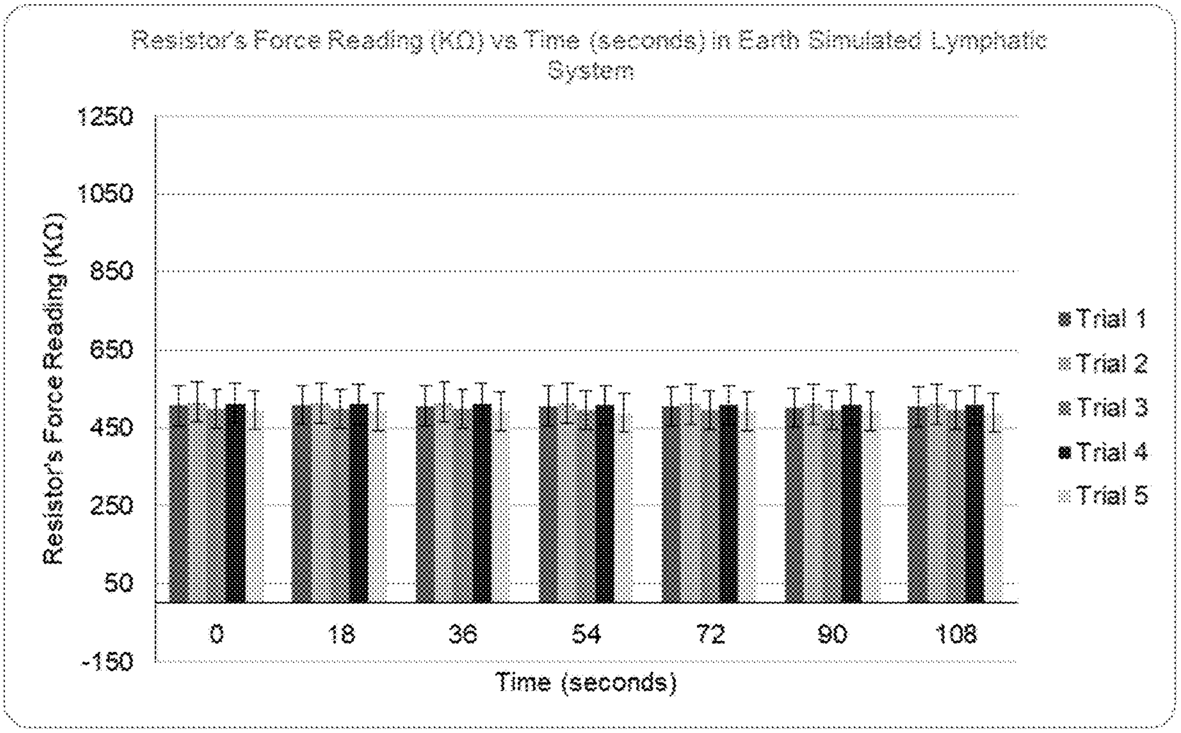
FIG. 3A is a graph showing force resistor readings (KΩ) vs. time (seconds) during the Earth-simulated trials described in Example 1.
Figure 3B:
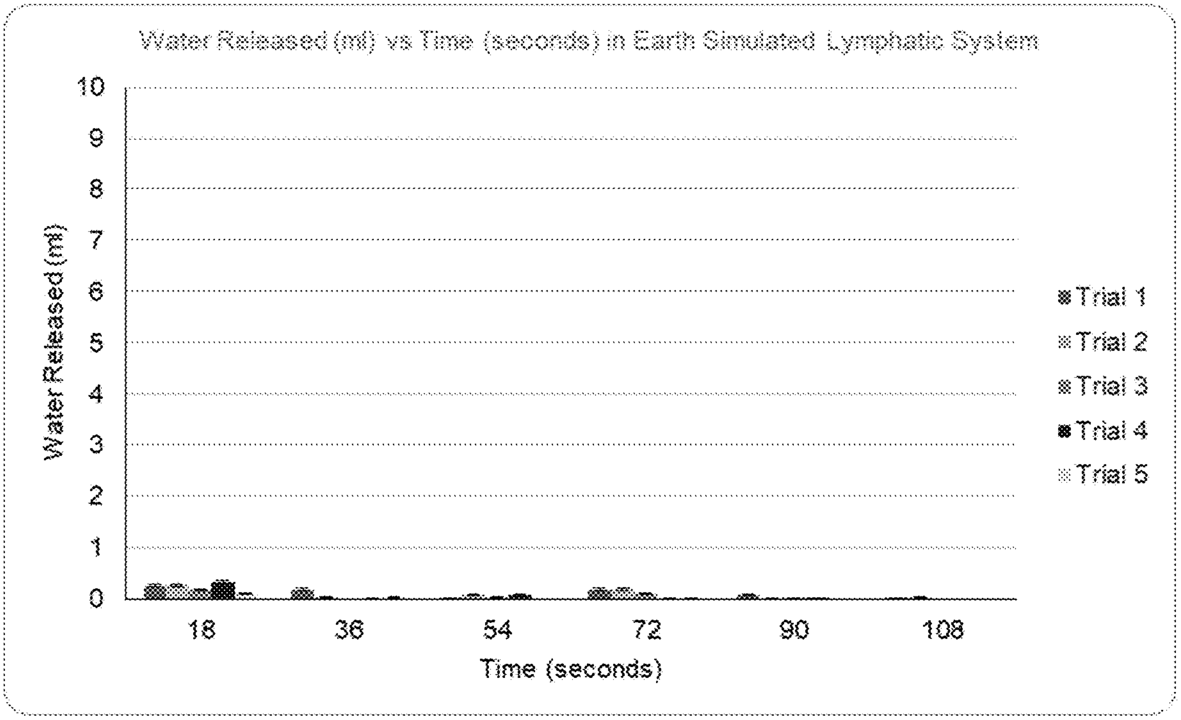
FIG. 3B is a graph showing water released (mL) vs. time (seconds) during the Earth-simulated trials described in Example 1.
Figure 4:
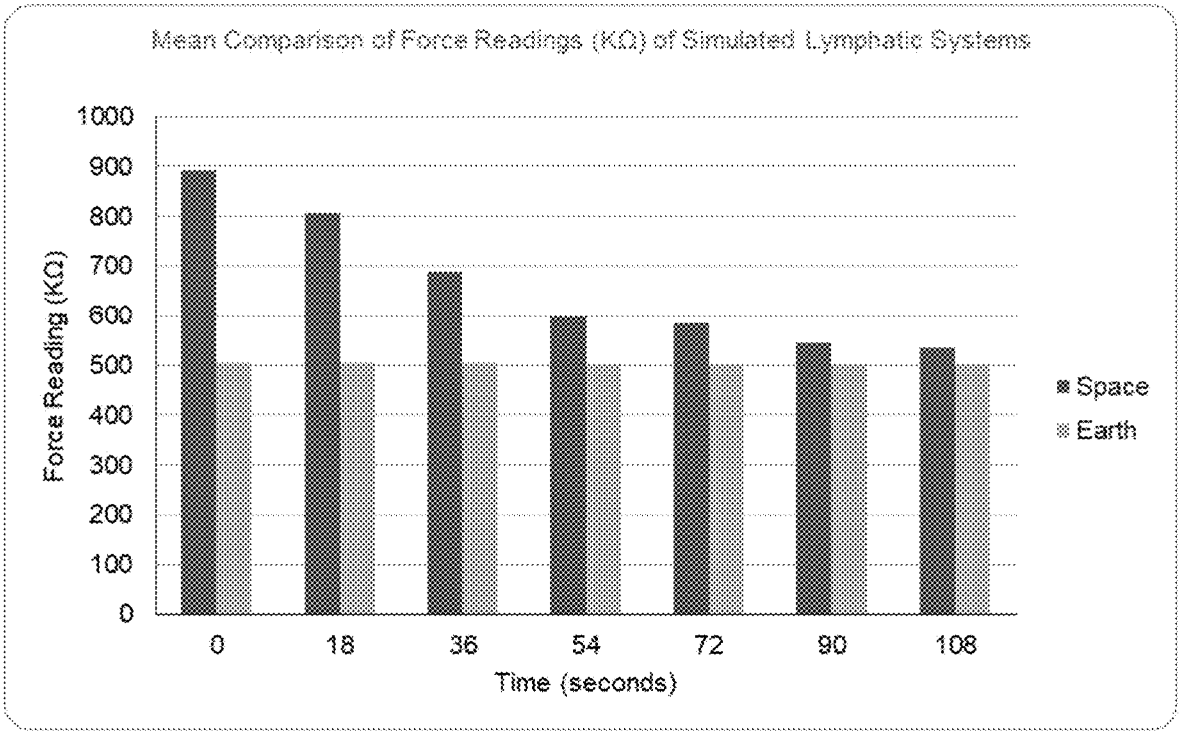
FIG. 4 is a graph showing a comparison of force resistor readings (KΩ) from the space-simulated and Earth-simulated trials described in Example 1.

The data from the "Space" trials are provided in Tables 1-3 and FIGS. 2A and 2B and the data from the "Earth" trials are provided in Tables 4-6 and FIGS. 3A and 3B. A comparison of the force readings between the "Space" and "Earth" trials is provided in FIG. 4. The "Space" trials demonstrated that the LCSS effectively removed liquid from the sponges representing swollen tissue experiencing lymph build-up, suggesting that the device will also be effective in removing lymph from swollen tissue. Meanwhile, there was much less water released during the "Earth" trials, demonstrating that the LCSS would not remove lymph from tissues that are not swollen or experiencing build-up of lymph fluid.

TABLE 1

Initial and Final Weights During "Space" Trials 1-5

| | Trial 1 | Trial 2 | Trial 3 | Trial 4 | Trial 5 |
|---|---|---|---|---|---|
| Initial Weight (g) | 60.38 | 58.24 | 65.04 | 65.70 | 68.40 |
| Final Weight (g) | 49.28 | 48.71 | 51.4 | 46.92 | 52.32 |

TABLE 2

Forces Recorded During "Space" Trials 1-5

| | Time (seconds) | Trial 1 | Trial 2 | Trial 3 | Trial 4 | Trial 5 |
|---|---|---|---|---|---|---|
| Force (KΩ) | 0 | 838 | 834 | 925 | 927 | 939 |
| | 18 | 793 | 810 | 797 | 771 | 862 |
| | 36 | 663 | 738 | 622 | 620 | 804 |
| | 54 | 530 | 582 | 602 | 601 | 672 |
| | 72 | 532 | 571 | 593 | 608 | 621 |
| | 90 | 523 | 535 | 569 | 535 | 572 |
| | 108 | 521 | 525 | 553 | 518 | 561 |

TABLE 3

Water Released During "Space" Trials 1-5

| | Time (seconds) | Trial 1 | Trial 2 | Trial 3 | Trial 4 | Trial 5 |
|---|---|---|---|---|---|---|
| Water Released (mL) | 18 | 6.69 | 4.00 | 7.98 | 8.68 | 6.88 |
| | 36 | 4.52 | 2.35 | 3.95 | 4.39 | 3.50 |
| | 54 | 3.53 | 3.46 | 2.70 | 1.10 | 3.37 |
| | 72 | 1.42 | 0.93 | 0.87 | 0.7 | 2.85 |
| | 90 | 0.23 | 1.53 | 1.23 | 2.29 | 2.73 |
| | 108 | 0.3 | 0.5 | 0.8 | 1.23 | 0.7 |

TABLE 4

Initial and Final Weights During "Earth" Trials 1-5

| | Trial 1 | Trial 2 | Trial 3 | Trial 4 | Trial 5 |
|---|---|---|---|---|---|
| Initial Weight (g) | 39.93 | 43.51 | 32.32 | 40.47 | 29.04 |
| Final Weight (g) | 39.51 | 42.91 | 31.79 | 40.21 | 29.00 |

TABLE 5

Forces Recorded During "Earth" Trials 1-5

| | Time (seconds) | Trial 1 | Trial 2 | Trial 3 | Trial 4 | Trial 5 |
|---|---|---|---|---|---|---|
| Force (KΩ) | 0 | 508 | 517 | 499 | 513 | 496 |
| | 18 | 509 | 515 | 499 | 511 | 492 |
| | 36 | 507 | 516 | 500 | 513 | 494 |
| | 54 | 507 | 514 | 496 | 509 | 491 |
| | 72 | 506 | 512 | 495 | 509 | 493 |
| | 90 | 503 | 512 | 495 | 510 | 493 |
| | 108 | 505 | 511 | 497 | 509 | 491 |

TABLE 6

Water Released During "Earth" Trials 1-5

| | Time (seconds) | Trial 1 | Trial 2 | Trial 3 | Trial 4 | Trial 5 |
|---|---|---|---|---|---|---|
| Water Released (mL) | 18 | 0.26 | 0.27 | 0.18 | 0.33 | 0.11 |
| | 36 | 0.19 | 0.04 | 0.01 | 0.02 | 0.04 |
| | 54 | 0.03 | 0.09 | 0.04 | 0.09 | 0.00 |
| | 72 | 0.19 | 0.20 | 0.11 | 0.02 | 0.02 |
| | 90 | 0.08 | 0.02 | 0.03 | 0.03 | 0.00 |
| | 108 | 0.03 | 0.04 | 0.00 | 0.01 | 0.00 |

Example 2. Additional Testing

Additional "Space" and "Earth" trials were conducted according to the procedure described in Example 1. Tables providing data from these additional trials are provided in Tables 7-12 below. The data observed in the additional tests all showed similar trends as the initial tests conducted in Example 1. These additional trials also show that the LCSS was effective at removing liquid from the swollen "Space"

sponges, suggesting that the device will be effective in removing lymph from swollen tissue.

TABLE 7

| Initial and Final Weights During "Space" Trials 6-10 | | | | | |
|---|---|---|---|---|---|
| | Trial 1 | Trial 2 | Trial 3 | Trial 4 | Trial 5 |
| Initial Weight (g) | 67.26 | 65.57 | 58.37 | 64.23 | 59.84 |
| Final Weight (g) | 54.70 | 59.64 | 53.00 | 61.03 | 56.44 |

TABLE 8

| Forces Recorded During "Space" Trials 6-10 | | | | | | |
|---|---|---|---|---|---|---|
| | Time (seconds) | Trial 1 | Trial 2 | Trial 3 | Trial 4 | Trial 5 |
| Force (KΩ) | 0 | 909 | 889 | 639 | 854 | 790 |
| | 18 | 832 | 835 | 601 | 831 | 729 |
| | 36 | 740 | 789 | 591 | 832 | 699 |
| | 54 | 692 | 742 | 582 | 839 | 709 |
| | 72 | 658 | 691 | 584 | 810 | 682 |
| | 90 | 639 | 660 | 581 | 802 | 681 |
| | 108 | 602 | 644 | 577 | 801 | 677 |

TABLE 9

| Water Released During "Space" Trials 6-10 | | | | | | |
|---|---|---|---|---|---|---|
| | Time (seconds) | Trial 1 | Trial 2 | Trial 3 | Trial 4 | Trial 5 |
| Water Released (mL) | 18 | 4.59 | 4.19 | 1.23 | 4.01 | 2.42 |
| | 36 | 5.50 | 1.39 | 0.4 | 0.1 | 1.18 |
| | 54 | 1.13 | 1.05 | 0.3 | 0.0 | 0.0 |
| | 72 | 0.7 | 1.87 | 0.0 | 0.20 | 1.99 |
| | 90 | 0.3 | 0.5 | 0.1 | 0.0 | 0.0 |
| | 108 | 0.3 | 0.2 | 0.0 | 0.0 | 0.0 |

TABLE 10

| Initial and Final Weights During "Earth" Trials 6-10 | | | | | |
|---|---|---|---|---|---|
| | Trial 1 | Trial 2 | Trial 3 | Trial 4 | Trial 5 |
| Initial Weight (g) | 27.77 | 41.00 | 44.38 | 32.47 | 43.45 |
| Final Weight (g) | 27.49 | 39.27 | 41.96 | 32.39 | 41.72 |

TABLE 11

| Forces Recorded During "Earth" Trials 6-10 | | | | | | |
|---|---|---|---|---|---|---|
| | Time (seconds) | Trial 1 | Trial 2 | Trial 3 | Trial 4 | Trial 5 |
| Force (KΩ) | 0 | 421 | 510 | 533 | 489 | 531 |
| | 18 | 422 | 499 | 527 | 483 | 523 |
| | 36 | 418 | 502 | 529 | 484 | 523 |
| | 54 | 418 | 499 | 526 | 483 | 535 |
| | 72 | 410 | 498 | 527 | 485 | 524 |
| | 90 | 408 | 501 | 530 | 484 | 520 |
| | 108 | 410 | 500 | 529 | 484 | 521 |

TABLE 12

| Water Released During "Earth" Trials 6-10 | | | | | | |
|---|---|---|---|---|---|---|
| | Time (seconds) | Trial 1 | Trial 2 | Trial 3 | Trial 4 | Trial 5 |
| Water Released (mL) | 18 | 0.1 | 0.4 | 0.8 | 0.0 | 0.1 |
| | 36 | 0.0 | 0.0 | 0.1 | 0.0 | 0.0 |
| | 54 | 0.0 | 0.0 | 0.0 | 0.1 | 0.00 |
| | 72 | 0.1 | 0.0 | 0.1 | 0.0 | 0.1 |
| | 90 | 0.0 | 0.0 | 0.0 | 0.0 | 0.0 |
| | 108 | 0.1 | 0.0 | 0.0 | 0.0 | 0.0 |

It is to be understood that while the invention has been described in conjunction with the various illustrative embodiments, the forgoing description is intended to illustrate and not limit the scope of the invention, which is defined by the scope of the appended claims. For example, a variety of systems and/or methods may be implemented based on the disclosure and still fall within the scope of the invention. Other aspects, advantages, and modifications are within the scope of the following claims.

What is claimed is:

1. A device for promoting circulation of lymphatic fluid in a human subject comprising:

an elastic tubular bandage configured to be fitted to an arm of the human subject;

two force-sensing resistors configured to detect a force exerted by the arm of the human subject;

eight coin-type vibrational motors rated for a speed of 12,000 RPM, a voltage of 3 V, and a current of 85 mA; and a controller comprising an Arduino coupled with the force-sensing resistors and the coin-type vibrational motors;

wherein the controller is configured to activate the coin-type vibrational motors in response to the force-sensing resistors detecting the force above about 600 kΩ and deactivate the coin-type vibrational motors in response to the force-sensing resistors detecting the force falling below about 600 kΩ.

2. A method of promoting circulation of lymphatic fluid or treating lymphedema in a human subject, wherein the method comprises fitting the device of claim 1 onto a body part of the human subject.

3. The method of claim 2, wherein the human subject is in a reduced gravity environment.

4. The method of claim 2, wherein the human subject is an astronaut.

5. The method of claim 2, wherein the method is used in combination with an additional therapy for treating lymphedema or promoting circulation of lymph fluid comprising exercise, drug therapy, or laser therapy.

6. The device of claim 1, wherein the eight coin-type vibrational motors are activated in pairs, with a time delay between the activation of each pair.

7. The device of claim 6, wherein the time delay is three seconds.

8. The device of claim 1, wherein the two force-sensing resistors, eight coin-type vibrational motors, and controller are connected via at least one connecting wire.

9. The device of claim 8, further comprising a heat seal around the at least one connecting wire.

10. The device of claim 1, wherein the elastic tubular bandage is comprised of a material selected from cotton, Nylon, spandex, or a combination thereof.

11. The device of claim 1, wherein the elastic tubular bandage has a circumference of from about 10 inches to about 22 inches.

12. The device of claim 1, wherein the force exerted by the arm of the human subject is a result of swelling of the arm of the human subject caused by build-up of lymphatic fluid or lymphedema.

13. The device of claim 1, wherein the eight coin-type vibrational motors are distributed evenly across the surface of the elastic tubular bandage.

14. The device of claim 1, wherein the eight coin-type vibrational motors are activated simultaneously.

15. The device of claim 1, wherein each of the eight coin-type vibrational motors is activated individually with a time delay between each activation.

16. The device of claim 1, wherein the two force-sensing resistors, eight coin-type vibrational motors, and controller are connected wirelessly.

* * * * *